United States Patent [19]

Sampathkumar

[11] Patent Number: 4,716,035

[45] Date of Patent: Dec. 29, 1987

[54] ORAL COMPOSITIONS AND METHODS FOR TREATING GINGIVITIS

[75] Inventor: Padmini Sampathkumar, Fairfield, Ohio

[73] Assignee: The Procter & Gamble Company, Cincinnati, Ohio

[21] Appl. No.: 912,728

[22] Filed: Sep. 26, 1986

Related U.S. Application Data

[60] Continuation-in-part of Ser. No. 738,103, May 24, 1985, Pat. No. 4,670,252, and a continuation-in-part of Ser. No. 811,148, Dec. 19, 1985, Division of Ser. No. 811,149, Dec. 19, 1985.

[51] Int. Cl.$^4$ .................. A61K 7/16; A61K 7/18; A61K 9/68
[52] U.S. Cl. ...................... 424/52; 424/53; 514/859; 514/900; 514/901; 514/902
[58] Field of Search .................. 424/52, 53; 514/859, 514/900, 901, 902

[56] References Cited

U.S. PATENT DOCUMENTS

| | | | |
|---|---|---|---|
| 3,988,433 | 10/1976 | Benedict | 424/53 |
| 4,350,681 | 9/1982 | Fulton | 424/53 |
| 4,385,008 | 5/1983 | Hignett | 260/502 R |
| 4,403,994 | 9/1983 | Hignett | 8/111 |
| 4,483,781 | 11/1984 | Hartman | 252/174.12 |
| 4,490,269 | 12/1984 | Gallopo | 252/94 |

FOREIGN PATENT DOCUMENTS

| | | |
|---|---|---|
| 27693 | 4/1981 | European Pat. Off. . |
| 96525 | 12/1983 | European Pat. Off. . |
| 133354 | 2/1985 | European Pat. Off. . |
| 1477691 | 10/1977 | United Kingdom . |
| 2137882 | 10/1984 | United Kingdom . |

OTHER PUBLICATIONS

Merka et al., "Disinfectant Properties of Some Peroxide Compounds," Voenno–Med. Zh., vol. 2, pp. 46–50 (1967); Chemical Abstracts 67: 67542e.

*Primary Examiner*—Shep K. Rose
*Attorney, Agent, or Firm*—Kim William Zerby; George W. Allen; Jack D. Schaeffer

[57] ABSTRACT

This invention relates to oral compositions comprising certain organic peroxy acid antigingivitis agents and a source of $F^-$ fluoride ions as an anticaries agent. Organic peroxy acid-based antigingivitis agents useful in the present invention include monoperphthalic acid and its derivatives, and 1,12-dodecanedioic peroxy acid and its derivatives. Sources of $F^-$ fluoride ions for use in the present invention include sodium fluoride, stannous fluoride, strontium fluoride, indium fluoride, and amine fluorides.

The present invention further relates to methods for treating or preventing diseases of the oral cavity in humans or lower animals with reduced staining of the teeth or dentures. These methods comprise topically applying to the oral surfaces of the human or lower animal a safe and effective amount of a composition of the present invention.

20 Claims, No Drawings

ORAL COMPOSITIONS AND METHODS FOR TREATING GINGIVITIS

CROSS REFERENCE TO RELATED APPLICATIONS

This application is a continuation-in-part of Pat. No. prior applications Ser. No. 738,103, filed May 24, 1985; now GS, 4,670,252 Ser. No. 811,148, filed Dec. 19, 1985; and Ser. No. 811,149, filed Dec. 19, 1985.

BACKGROUND OF THE INVENTION

The present invention relates to oral compositions containing certain organic peroxy acid-based antigingivitis agents and a particular type of fluorine-containing compound as an anticaries agent. The present invention further relates to methods for treating or preventing diseases of the oral cavity, which methods result in little or no staining of the teeth.

Organic peroxy acid compounds are known generally to be useful as both bleaching agents and antibacterial agents. For example, U.S. Pat. No. 3,988,433, to Benedict, issued Oct. 26, 1976, discloses that certain alkyl diperoxy acids, and meta- or para-substituted aromatic peroxy acids, are useful for preventing or removing stains from teeth. These same organic peroxy acids are also said to be antibacterial agents for controlling the bacterial population in the mouth.

In spite of such disclosures, and in spite of the large amount of research exerted to develop better antibacterial agents suitable for oral use, there is a continuing need to identify additional antibacterial oral compositions which are effective for treating or preventing oral diseases, such as gingivitis and periodontal disease, and which may also provide an anticaries benefit. The antibacterial actives in such oral compositions should cause little or no tooth stain.

It is therefore an object of the present invention to provide oral compositions which comprise certain organic peroxy acid-based antigingivitis agents in combination with certain fluorine-containing anticaries agents. It is a further object of the present invention to provide methods for treating or preventing diseases of the oral cavity in humans or lower animals by applying to the oral surfaces such a combination of an organic peroxy acid-based antigingivitis agent and a fluorine-containing anticaries agent. An additional object is to provide compositions and methods for treating diseases of the oral cavity which result in little or no staining of the teeth.

These and other objects of the present invention will be apparent from the detailed description of the invention contained hereinafter.

SUMMARY OF THE INVENTION

The present invention provides pharmaceutical compositions (e.g., toothpastes, tooth powders, mouth rinses, chewing gums, mouth sprays, lozenges, and sachets) useful for treating or preventing diseases of the oral cavity with reduced staining of teeth or dentures. These compositions comprise, by weight, from about 0.001% to about 99.9% of an organic peroxy acid-based antigingivitis agent selected from 1,12-dodecanedioic peroxy acid and its derivatives, monoperphthalic acid and its derivatives, and the pharmaceutically-acceptable salts and esters thereof. The compositions of the present invention further comprise from about 0.001% to about 10% by weight of a source of $F^-$ fluoride ions. This flouride ion source (e.g. sodium fluoride) in aqueous solution essentially completely dissociates to provide free $F^-$ fluoride ions in solution. Finally, the compositions of the present invention further comprise a pharmaceutically-acceptable carrier suitable for delivering the antigingivitis agent and fluoride ion source to the oral surfaces.

The present invention also relates to methods for treating or preventing diseases of the oral cavity in humans or lower animals with reduced staining of the teeth or dentures. These methods comprise topically applying (e.g., by rinsing or brushing or masticating) to the oral surfaces of the human or lower animal a safe and effective amount of a composition of the present invention.

DETAILED DESCRIPTION OF THE INVENTION

Oral Compositions (a) Organic Peroxy Acid-Based Antigingivitis Agents:

The organic peroxy acid-based antigingivitis agents which are useful in the oral compositions of the present invention are 1,12-dodecanedioic peroxy acid and derivatives thereof, monoperphthalic acid and derivatives thereof, and the pharmaceutically-acceptable salts and esters thereof. Preferred are the monoperphthalic acid derivatives, and especially magnesium monoperphthalate.

The 1,12-dodecanedioic peroxy acid-based antigingivitis agents may be unsubstituted or substituted. The substituted 1,12-dodecanedioic peroxy acid antigingivitis agents may be substituted with one or more substituents selected from the group consisting of straight or branched chain alkyl groups having from 1 to about 6 carbon atoms (preferably methyl or ethyl), phenyl, benzyl, chloro, fluoro, nitro, trifluoromethyl, trialkylammonium (e.g., trimethylammonium, triethylammonium), —$CO_2H$, —$CO_3H$, or mixtures thereof. Preferably, no more than about two of the carbon atoms in the 1,12-dodecanedioic acid chain is substituted.

Most preferably, the 1,12-dodecanedioic acid chain is unsubstituted (i.e., —$(CH_2)_{10}$—). It is further preferred that the 1,12-dodecanedioic acid antigingivitis agent be the diperoxy acid (i.e., $HO_3C(CH_2)_{10}CO_3H$). However, it is to be understood that a peroxy acid of unsubstituted or substituted 1,12-dodecanedioic acid may also be a compound having only one peroxy acid group per molecule at either the 1 or 12 position, provided there is a carboxylic acid or carboxylate group at the other end of the carbon chain, e.g., $HO_2C(CH_2)_{10}CO_3H$. The oral compositions herein may also comprise mixtures of diperoxy and monoperoxy 1,12-dodecanedioic acid, and/or the pharmaceutically-acceptable salts or esters of such acids.

The 1,12-dodecanedioic peroxy acid antigingivitis agents of the present invention are known compounds. They may be synthesized by known methods such as methods disclosed in, e.g., U.S. Pat. No. 4,483,781, to Hartman, issued Nov. 20, 1984; and in U.S. Pat. No. 3,988,433, to Benedict, issued Oct. 26, 1976. The disclosures of both these patents are incorporated herein by reference in their entirety.

The monoperphthalic acid-based antigingivitis agents are substituted or unsubstituted monoperphthalic acid derivatives having the general structure:

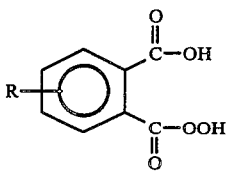

wherein R is one or more substituents independently selected from the group consisting of hydrogen, straight or branched chain saturated alkyl having from 1 to about 20 carbon atoms (e.g., methyl, ethyl), phenyl, benzyl, naphthyl, chloro, fluoro, nitro, sulphonate, trifluoromethyl, —NR'$_3$, —CO$_2$H, —CO$_3$H, —OCOR', and —OR'; with each R' being independently selected from straight or branched chain saturated alkyl having from 1 to about 6 carbon atoms (preferably R' is ethyl or, especially, methyl); or the pharmaceutically-acceptable salts or esters thereof. Preferred R groups are hydrogen, straight or branched chain saturated alkyl having from 1 to about 20 carbon atoms, phenyl, benzyl, chloro, fluoro, —CO$_2$H and —OR'. Particularly preferred is all R groups being hydrogen.

Most preferred for use in the oral compositions of the present invention is the magnesium salt of monoperphthalic acid. This magnesium salt is the salt of the carboxylic acid group only, having the formula:

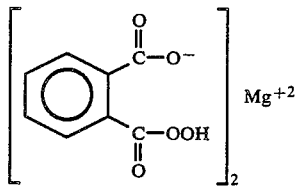

as disclosed in European Patent Application No. 27,693, published Apr. 29, 1981, filed by Interox Chemicals, Ltd., the disclosure of which is incorporated herein by reference in its entirety. This compound is a hydrate when in its solid form.

Synthesis of substituted and unsubstituted monoperphthalic acid derivatives can be achieved by those skilled in the art using methods disclosed in, for example, European Patent Application No. 27,693, published Apr. 29, 1981, filed by Interox Chemicals, Ltd.; European Patent Application No. 66,992, to Interox Chemicals, Ltd.; U.S. Pat. No. 3,075,921, to Brockelhurst, et al.; "Organic Peroxides", Daniel Swern, Editor, published 1970 by John Wiley & Sons, Inc.; and in British Patent Specification No. 1,378,671; the disclosures of all of which being incorporated herein by reference in their entirety. Synthesis of the magnesium salt of monoperphthalic acid is disclosed in the European Patent Application No. 27,693, incorporated by reference hereinbefore. This compound is also commercially available from Interox Chemicals Limited, London, England.

The term "pharmaceutically-acceptable salts or esters", as used herein relative to the organic peroxy acid-based antigingivitis agents, means esters and salts of the organic peroxy acid antigingivitis agents described hereinbefore which have the same general antibacterial properties as the acid form, and which are acceptable from a toxicity viewpoint. Nonlimiting examples of pharmaceutically-acceptable salts include alkali metal (e.g., sodium, potassium), alkaline earth mineral (e.g., calcium, magnesium), nontoxic heavy metals, and trialkylammonium (e.g., trimethylammonium). Nonlimiting examples of pharmaceutically-acceptable esters include the methyl and ethyl esters. Preferred are the pharmaceutically-acceptable salts of divalent cations (e.g., magnesium, calcium), and most preferred is the magnesium salt.

The organic peroxy acid-based antigingivitis agents will generally comprise from about 0.001% to about 99.9% by weight of the oral compositions of the present invention, more preferably from about 0.01% to about 50% by weight of the compositions, and from about 0.1% to about 35% by weight of the compositions being most preferred. Depending on the form of the oral composition (e.g., tablet; paste; solution) and the intended use of the composition (e.g., toothpaste; mouth rinse), preferred concentrations of the organic peroxy acid-based antigingivitis agent will fall within ranges more narrowly set for these individual types of compositions. Preferred concentration ranges for such particular types of compositions are discussed in greater detail hereinafter.

(b) Source of F$^-$ Fluoride Ions

The oral compositions of the present invention further essentially comprise a source of F$^-$ fluoride ions. Such a source of F$^-$ fluoride ions serves as an anticaries agent and can also reduce the possibility of the oral compositions herein staining teeth. The term "source of F$^-$ fluoride ions", as used herein, means a fluoride-containing salt which in aqueous solution essentially completely dissociates to provide free F$^-$ fluoride ion after 10 minutes when measured by a F$^-$ fluoride ion electrode. The selection of the source of F$^-$ fluoride ions for use in the oral compositions of the present invention may therefore be easily made from the various inorganic and organic fluoride compounds available for use in oral compositions after a simple analysis. Fluoride compounds from which the source of F$^-$ fluoride ions may be selected by analysis are described, for example, in U.S. Pat. No. 3,535,421, Briner and Widder, issued Oct. 20, 1970, the disclosure of which is incorporated by reference in its entirety herein. Suitable sources of F$^-$ fluoride ions include, for example, sodium fluoride, stannous fluoride, strontium fluoride, indium fluoride, and amine fluorides. Preferred are stannous fluoride and sodium fluoride. Most preferred is sodium fluoride.

The percent dissociation into free F$^-$ fluoride ion of a fluoride-containing compound in aqueous solution may be determined by measuring the F$^-$ fluoride ion concentration (10 minutes after mixing the compound with water) using, for example, an ORION fluoride selective electrode and an ORION model 601A or EA$^R$ 940 digital ion analyzer (from Orion Research Incorporated, Cambridge, Mass.). The use of this equipment to measure F$^-$ fluoride ion concentration is described more fully in the instruction manual for this equipment (e.g., "EA$^R$ 940 Expandable IonAnalyzer Instruction Manual", Orion Research Incorporated, Cambridge, Mass. 1985, the disclosure of which is incorporated by reference in its entirety herein), and in the Examples provided hereinafter. Techniques useful for performing F$^-$ fluoride ion concentration analyses are also described in "Orion U.S. Ion-Selective Electrode Catalog and Guide to Ion Analysis", Orion Research Incorporated (Cambridge, Mass.; 1986; hereinafter referred to as "Orion Catalog 1986"), and in Lindahl, "Fluoride and Monofluorophosphate Analysis", Caries Research, Vol. 17, Suppl. 1, pp. 9–15 (1983), the disclosures of both these references being incorporated by reference in its entirety herein.

The source of $F^-$ fluoride ions will generally comprise from about 0.001% to about 10% by weight of the oral compositions of the present invention, more preferably from about 0.001% to about 5% by weight of the compositions, and most preferably from about 0.005% to about 2% by weight of the compositions. Molar ratios for the source of $F^-$ fluoride ions to organic peroxy acid-based antigingivitis agent are preferably from about 0.01:1 to about 1000:1, and more preferably from about 0.1:1 to about 100:1. The most preferred ratio is 1:1 when magnesium monoperphthalate is utilized, and 2:1 when diperoxy dodecanedioic acid is utilized. As for the organic peroxy acid-based antigingivitis agent described hereinbefore, the preferred concentrations of the source of $F^-$ fluoride ion will fall within ranges more narrowly set for the individual types of compositions utilized. Preferred concentrations for the source of $F^-$ fluoride ion are discussed in greater detail hereinafter.

(c) Pharmaceutically-acceptable Carrier

In addition to the organic peroxy acid-based antigingivitis agent and the source of $F^-$ fluoride ions, the oral compositions herein essentially contain a pharmaceutically-acceptable carrier for the active components. The term "pharmaceutically-acceptable carrier", as used herein, means one or more compatible solid or liquid filler diluents or encapsulating substances which are suitable for delivering the combination of the organic peroxy acid-based antigingivitis agent and the source of $F^-$ fluoride ion to the oral cavity (e.g., the oral surfaces) of a human or lower animal.

The term "compatible", as used herein, means that the components of the carrier must be capable of being commingled with the actives and with each other in a manner such that there is no interaction which would substantially reduce during use the composition efficacy for treating or preventing diseases of the oral cavity. Pharmaceutically-acceptable carriers, of course, must be of sufficiently high purity and sufficiently low toxicity to render them suitable for administration to the oral cavity of the human or lower animal.

The oral compositions of the present contain pharmaceutically-acceptable carriers selected as appropriate for the method of composition administration. If the composition is to be used, e.g., as a mouth rinse for gingivitis, it is preferred that the composition be formulated with solid components that dissolve rapidly in the water (or, typically for mouth rinses, in an ethanol-water) media used to form a solution for administering the composition. Toothpaste, tooth powders, tooth gels, mouth sprays, lozenges, chewing gums, and sachets, would also be formulated such that they would be useful in the oral cavity.

Pharmaceutically-acceptable carriers can include the usual and conventional components of toothpaste, tooth powders, toothpaste gels, mouth rinses, mouth sprays, chewing gums, lozenges, and sachets as are more fully described hereinafter. Generally, however, the pharmaceutically-acceptable oral carriers should be materials which are free of reactive hydroxyl groups and normally also should be materials which do not contain other reactive sites, such as, for example, amino, amido, iodo, bromo, and sulfhydryl groups, and unsaturated, imino, and thioether linkages if the composition is to be stored for any appreciable length of time. Thus, it is preferred that the compositions of the present invention be totally or substantially anhydrous until just prior to use. Water can then be added to the composition just prior to use, for example, by dissolving the composition in water.

It is contemplated, however, that even reactive carriers may be used in formulating the oral compositions of the present invention when the reactive carrier is partitioned (e.g., by encapsulation) or stored separately from the organic peroxy acid-based antigingivitis agent, and the product is used immediately after the components are combined. For example, toothpaste compositions conventionally contain abrasive materials, sudsing agents, binders, humectants, flavoring and sweetening agents. Most of these cannot be maintained in contact with the organic peroxy acid-based antigingivitis agent for substantial periods of time. Therefore, components of toothpast compositions of the present invention will normally be partitioned in separate containers or chambers, to be combined just before use. Compatible additives and actives, including the source of $F^-$ fluoride ions, may be combined with the organic peroxy acid-based antigingivitis agent-containing component of the compositions herein.

Dentifrice compositions (e.g., toothpastes; tooth gels; and tooth powders) generally comprise, in addition to the organic peroxy acid-based antigingivitis agent and source of $F^-$ fluoride ions, a pharmaceutically-acceptable carrier which can comprise the usual and conventional components of dentifrice compositions. U.S. Pat. No. 3,988,433, to Benedict, issued Oct. 26, 1976 provides specific disclosure of such usual and conventional pharmaceutically-acceptable dentifrice composition carriers. The disclosure of this patent is incorporated herein by reference in its entirety. Generally the dentifrices of the present invention may include abrasive polishing material, flavoring agent, sweetening agent, coloring agent, emulsifying agent, thickening agent, humectant, alcohol, chelating agent, and/or water, with any carrier unsuitable for storage stability when combined with the organic peroxy acid-based antigingivitis agent being stored separately as noted hereinbefore.

Typically, the organic peroxy acid-based antigingivitis agent will generally comprise from about 0.01% to about 50%, preferably from about 0.01% to about 35%, and more preferably from about 1% to about 35% by weight of the oral compositions of the present invention in the form of a dentifrice. Also, the typical dentifrice composition will contain a source of $F^-$ fluoride ions which comprises from about 0.001% to about 10%, preferably from about 0.001% to about 5%, and more preferably from about 0.005% to about 2% by weight of the dentifrice composition. Finally, the pharmaceutically-acceptable carrier components of the dentifrice compositions will generally comprise from about 50% to about 99.99%, preferably from about 65% to about 99.99%, and more preferably from about 65% to about 99% by weight of the dentifrice composition.

Mouth rinse compositions of the present invention are frequently in the form of anhydrous solid powder, tablet, or capsule concentrates which dissolve rapidly in water. Mouth rinse compositions may also be in the form of an ethanol-water mixture (ethanol:water ratio from about 1:20 to about 1:2 on a volume to volume basis; preferred being 15% ethanol solution). It is also preferred that the concentrate be formulated to include as part of the pharmaceutically-acceptable carrier an effervescing agent and/or surfactant (preferably a nonionic surfactant) to facilitate rapid disintegration of the solid and dissolution into the aqueous carrier, as well as a chelating agent. Preferred effervescing agents are mixtures of carbonate and citrate, or bicarbonate and citrate. The present invention includes both the mouth rinse concentrate and the aqueous mouth rinse solution.

Mouth rinse compositions generally comprise in addition to the organic peroxy acid-based antigingivitis agent a pharmaceutically-acceptable carrier which can comprise other ingredients which are typically found in mouth rinses, e.g., flavoring and sweetening agents, humectants, sudsing agents, coloring agents, etc., as well as the above-noted effervescing agents. As noted hereinbefore, it may be necessary to keep some or all of the pharmaceutically-acceptable carrier components separated from the organic peroxy acid-based antigingivitis agent until just prior to use in order to preserve the storage stability of the composition. U.S. Pat. No. 3,988,433, to Benedict, issued Oct. 26, 1976, provides disclosure concerning the preparation of mouth rinse compositions of the type contemplated by the present invention. The disclosure of this patent is incorporated herein by reference.

Typically, anhydrous mouth rinse concentrate compositions of the present invention comprise organic peroxy acid-based antigingivitis agent, a source of $F^-$ fluoride ion, and a pharmaceutically-acceptable carrier in the same concentrations as in the dentitrice compositions described hereinbefore. In addition, aqueous mouth rinse solutions of the present invention may comprise organic peroxy acid-based antigingivitis agents in an amount of from about 0.001% to about 10%, more preferably from about 0.01% to about 5%, and most preferably from about 0.05% to about 3%, by weight of the composition. The source of $F^-$ fluoride ion in these aqueous compositions may comprise from about 0.001% to about 10%, more preferably from about 0.001% to about 5%, and most preferably from about 0.005% to about 2% by weight of the composition. The aqueous carrier in such compositions may generally comprise ethanol/water mixtures, and may be present in amount of from about 90% to about 99.99%, more preferably from about 95% to about 99.9%, and most preferably from about 97% to about 99.5%, by weight of the composition.

Preparation of compositions of the present invention in the form of mouth sprays, lozenges, chewing gums, sachets, creams, gels, powders, etc., can readily be achieved by one of ordinary skill in the art using the teachings disclosed hereinbefore and the teachings in, for example, U.S. Pat. No. 3,988,433, to Benedict; U.S. Pat. No. 4,472,373, to Lyons; and U.S. Pat. No. 4,083,955, to Grabenstetter et al., all of which are incorporated herein by reference in their entirety.

Additionally, as part of the pharmaceutically-acceptable carrier of these oral compositions of the present invention which contain a 1,12-dodecanedioic peroxy acid antigingivitis agent, it is preferred that the compositions comprise a boron-containing stabilizing agent for the peroxy acid. This boron-containing material is capable of significantly retarding the rate of hydrolytic decomposition of this aliphatic peroxy acid-based antigingivitis agent when the compositions herein are dissolved in an aqueous solution having a pH between about 5 and about 10. Generally, this boron-containing, aliphatic peroxy acid-stabilizing agent will be a compound having a boron to oxygen bond wherein the oxygen atom in this boron-oxygen combination is either partially or wholly in the anionic form in aqueous solution. Thus, boron-containing compounds useful as stabilizing agents in the compositions of the present invention are those which, in aqueous solution, typically yield the ionic functional group $B-O^-$.

Particularly preferred boron-containing, aliphatic peroxy acid-stabilizing agents useful in the oral compositions of the present invention are boric acid (i.e., $H_3BO_3$), and its pharmaceutically-acceptable salts or esters (e.g., $NaH_2BO_3$; $Na_2HBO_3$); pyroboric acid (i.e., $H_2B_4O_7$), and its pharmaceutically-acceptable salts or esters (e.g., $Na_2B_4O_7$, commercially known as "borax"); and boron-containing materials which generate boric acid and/or pyroboric acid, or their pharmaceutically-acceptable salts or esters, when contacted with water (e.g., boric oxide, which has the formula $B_2O_3$). The boron-containing, aliphatic peroxy acid-stabilizing agents must, of course, be of sufficiently high purity and sufficiently low toxicity to make them suitable for administration to the oral cavity of a human or lower animal.

The term "pharmaceutically-acceptable salts or esters", as used herein relative to the aliphatic peroxy acid-stabilizing agents, means those salts or esters of the boron-containing, aliphatic peroxy acid-stabilizing agents which have the same general peroxy acid stabilizing properties as the acid, and which are acceptable from a toxicity viewpoint. Non-limiting examples of pharmaceutically-acceptable salts include alkali metal (i.e., sodium, potassium), alkaline earth metal (i.e., calcium, magnesium), non-toxic heavy metal, ammonium, and trialkyl ammonium (i.e., trimethyl ammonium) salts. Non-limiting examples of pharmaceutically-acceptable esters are methyl and ethyl esters.

For purposes of the present invention, the ratio of boron-containing aliphatic peroxy acid-stabilizing agent to 1,12-electrode dodecanedioic peroxy acid antigingivitis agent in the oral compositions herein should be such that in aqueous solution the rate of hydrolytic decomposition of the aliphatic peroxy acid antigingivitis agent is significantly retarded relative to the non-stabilized aqueous solution of the aliphatic peroxy acid antigingivitis agent. Frequently, a suitable ratio of boron-containing stabilizing agent to aliphatic peroxy acid antigingivitis agent can be expressed as a molar ratio which is based on the number of moles of boron atom relative to the number of moles of aliphatic peroxy acid groups. For example, if the pharmaceutical composition contains 1 mole of borax (i.e., $Na_2B_4O_7$) and 1 mole of diperoxy-1,12-dodecanedioic acid (i.e., $HO_3C(CH_2)_{10}CO_3H$), the molar ratio of boron atoms to aliphatic peroxy acid groups is 2:1 (4 moles of boron atoms per mole of borax: 2 moles of aliphatic peroxy acid groups per mole of diperoxy 1,12-dodecanedioic acid=2:1 molar ratio). Generally, this molar ratio of boron atoms to aliphatic peroxy acid moieties is at least about 0.01:1, preferably at least about 0.1:1, more preferably about 0.5:1, and most preferably at least about 1:1. The upper limit of such a boron atom to aliphatic peroxy acid moieties ratio will generally be about 1,000:1, preferably about 100:1, more preferably about 50:1, and most preferably about 10:1.

It is further preferred that the oral compositions of the present invention be formulated such that the aqueous solution, or aqueous environment, in which such oral compositions are used is maintained at a relatively constant pH within the range from about 5 to about 10, more preferably from about 7.0 to about 9.0, and most preferably from about 8.0 to about 9.0. Therefore, typically, the oral compositions of the present invention will contain a buffer within the pharmaceutically-acceptable carrier component. Non-limiting examples of buffers for use in the oral compositions of the present invention include citrate, citrate/bicarbonate, phosphate, and especially borate buffers.

Finally, it is preferred that a chelating agent (e.g., citrate) be included as part of the pharmaceutically-acceptable carrier. This is especially desirable for oral compositions which comprise magnesium monoperphthalate antigingivitis agent. It is more preferred that the molar ratio of chelating agent to organic peroxy acid antigingivitis agent be at least about 1:1 (i.e., equal to or greater amounts of chelating agent). Most preferred is citric acid:magnesium monoperphthalate in a molar ratio of about 1:1.

Method of Treating or Preventing Diseases of the Oral Cavity

The present invention also relates to a method for treating or preventing diseases of the oral cavity of humans or lower animals. Such a method comprises topically applying (e.g., by brushing or rinsing or masticating) to the oral surfaces of said human or lower animal a safe and effective amount of the combination of an organic peroxy acid-based antigingivitis agent and a source of $F^-$ fluoride ion.

The term "diseases of the oral cavity", as used herein, means diseases which are initiated and/or perpetuated by bacteria in the oral cavity, especially anaerobic bacteria, and includes such diseases as, for example, periodontal disease, gingivitis, periodontitis, gingivosis, periodontosis, periodontitis complex, and other inflammatory and/or degenerative conditions of the tissues within the oral cavity, plus caries, Vincent's disease, trench mouth, and malodor. Also, specifically included are dentoalveolar infections, dental abscesses (e.g., cellulitis of the jaw; osteomyelitis of the jaw), acute necrotizing ulcerative gingivitis (i.e., Vincent's infection), infectious stomatitis (i.e., acute inflammation of the buccal mucosa), and Noma (i.e., gangrenous stomatitis or cancrum oris). Oral and dental infections are more fully disclosed in Finegold, *Anaerobic Bacteria in Human Diseases*, chapter 4, pages 78-104, and chapter 6, pages 115-154 (Academic Press, Inc., New York, 1977), the disclosures of which are incorporated in their entirety herein by reference. The method of treatment of the present invention is particularly effective for treating or preventing periodontal disease, gingivitis and/or periodontitis.

The term "safe and effective amount", as used herein, means an amount of the organic peroxy acid-based antigingivitis agent and of the source of $F^-$ fluoride ion which is sufficient to significantly reduce the severity of the disease of the oral cavity being treated, but low enough to avoid serious side effects (at a reasonable benefit/risk ratio), within the scope of sound medical judgment. The safe and effective amount will vary with the particular infection being treated, the age and physical condition of the patient being treated, the severity of the infection, the duration of treatment, the nature of concomitant therapy, the specific form (i.e., acid, salt and/or ester) of the antigingivitis agent employed, the particular vehicle from which the combination is applied, and like factors within the knowledge and expertise of the attending physician or dentist.

Generally, for the diperoxy 1,12-dodecanedioic acid anti-gingivitis agent a safe and effective amount is greater than about $1 \times 10^{-4}$ grams of this antigingivitis agent per application, preferably within the range of from about $1 \times 10^{-4}$ grams to about 1 gram of the antigingivitis agent per application, more preferably from about $1 \times 10^{-4}$ grams to about 0.01 grams of diperoxy 1,12-dodecanedioic acid per application. In addition, the concentration of the 1,12-dodecanedioic acid antigingivitis agent in aqueous solutions may be in the range by weight of from about 0.001% to about 10% (about 1.2 ppm to about 12,000 ppm available oxygen ("A.O.") for diperoxy 1,12-dodecanedioic acid), preferably from about 0.001% to about 1% (about 1.2 ppm to about 1,200 ppm available oxygen for diperoxy 1,12-dodecanedioic acid), more preferred being from about 0.01% to about 1% (about 12 ppm to about 1,200 ppm available oxygen for diperoxy 1,12-dodecanedioic acid), with from about 0.05% to about 0.5% (about 60 ppm to about 600 ppm available oxygen for diperoxy 1,12-dodecanedioic acid) being most preferred.

Generally, the safe and effective amount of monoperphthalic acid antigingivitis agent which is taken into the oral cavity (based on equivalents of peroxide units per compound) is preferably from about $5 \times 10^{-6}$ moles to about $5 \times 10^{-3}$ moles, more preferred being from about $5 \times 10^{-6}$ moles to about $2 \times 10^{-3}$ moles, and most preferably from about $5 \times 10^{-5}$ moles to about $5 \times 10^{-4}$ moles. For the preferred magnesium salt of monoperphthalic acid, this is equivalent to from about 1 mg to about 1000 mg, with more preferred being from about 1 mg to about 400 mg, and from about 10 mg to about 100 mg most preferred. It is further preferred that the concentration of the monoperphthalic acid antigingivitis agent be such that the concentration of the available oxygen ("A.O.") in the medium that contacts the gingival tissue be in the range of from about 60 ppm to about 6000 ppm (from about 0.1% to about 10% by weight of 100% active magnesium monoperphthalate), with from about 240 ppm to about 3000 ppm more preferred (from about 0.4% to about 5% by weight of 100% active magnesium monoperphthalate), and from about 600 ppm to about 1800 ppm most preferred (from about 1% to about 3% by weight of 100% active magnesium monoperphthalate).

In order to effectively use the compositions of the present invention in the method of treatment of the present invention, it is generally necessary to apply such compositions within a relatively short period of time after exposing the organic peroxy acid antigingivitis agent-containing composition to water. For the rinse solutions of the present invention, it is preferred that they be utilized within about 30 seconds to about 1 minute after preparation of the aqueous solution to be applied. Time before application is generally less critical for other types of compositions of the present invention, for example, those compositions which ordinarily would be exposed to significant amounts of water only at the beginning of their use (e.g., tooth paste, chewing gums, lozenges). The period of time between hydration and use is also less important when a component of the pharmaceutically-acceptable carrier comprises a material which stabilizes the peroxy acid-based antibacterial agent against deactivation.

The following examples illustrate the oral compositions and methods of the present invention, and the benefits achieved by the utilization of such compositions and methods. These examples are illustrative of the invention herein and are not to be construed as limiting thereof.

EXAMPLE 1

Selection of Suitable Sources of F− Fluoride Ions

The percent dissociation of fluoride compounds into free F− fluoride ions after 10 minutes in aqueous solution is measured as follows. Fluoride measurements are made with an Orion fluoride selective electrode (Orion Catalog No. 940900, "Fluoride Solid-State, epoxy body electrode, U.S. standard connector", Orion Catalog 1986) using an Orion reference electrode (Orion Catalog No. 900100, "Epoxy body, Ag/AgCI internal", Orion Catalog 1986) and an Orion model 601A digital ionalyzer in the millivolt mode. Sample solutions are made at the time of measurement by adding the appropriate amount of water (approximately 20° C.) to the sample powder mix. Fluoride levels are measured within a minute of reconstitution (as soon as the powder appears to be in solution) and at various intervals up to ten minutes after reconstitution. The fluoride electrode response is compared to the appropriate electrode standard curve (which is prepared using a standardized fluoride solution such as the 100 ppm F− Fluoride Activity standard, Orion Catalog No. 940907, Orion Catalog 1986) to determine free fluoride levels.

Various fluoride-containing compounds and their percent dissociation in water after 10 minutes are listed in Table 1. As Table 1 illustrates, sodium fluoride, stannous fluoride and strontium fluoride are all essentially 100% dissociated after 10 minutes in water; thus these compounds are suitable sources of F− fluoride ions. By comparison, sodium monofluorophosphate and sodium fluorosilicate are essentially 0% dissociated after 10 minutes in water, and are not suitable sources of F− fluoride ions in the context of the present invention.

TABLE 1

Dissociation of fluoride-containing compounds in water

| Source of F−(*) | Theoretical F− | F− measured | % Dissociation |
|---|---|---|---|
| NaF | 0.226 mg/ml | 0.21 mg/ml | 100 |
| SnF$_2$ | 0.12 mg/ml | 0.11 mg/ml | 100 |
| SrF$_2$ | 0.15 mg/ml | 0.14 mg/ml | 100 |
| Na$_2$PO$_3$F | 0.066 mg/ml | 0.00 mg/ml | 0 |
| Na$_2$SiF$_6$ | 0.051 mg/ml | 0.00 mg/ml | 0 |

(*)Concentration in aqueous solution = 500 ppm.

EXAMPLE 2

Mouthrinse Compositions

Mouthrinse concentrate compositions (in solid form) of the present invention comprise the following components:

| Component | Composition A | Composition B |
|---|---|---|
| Magnesium monoperphthalate | 172 mg | 344 mg |
| Sodium carbonate | 200 mg | 470 mg |
| Citric acid | 170 mg | 340 mg |
| Sodium fluoride | 15 mg | 30 mg |

Mouthrinse compositions of the present invention are prepared by dissolving either concentrate composition A or B in 15 ml of water. Dissolution time is about one minute. The resulting mouthrinse solution contains 1% and 2%, respectively, of magnesium monoperphthalate (87% active). The A.O. concentration of these solutions is approximately 0.065 w/v and 0.13 w/v, respectively.

Rinsing for 30 seconds twice a day for 3 months with the aqueous mouthrinse obtained from composition A or B results in antigingivitis benefit and reduction in the number of pathogenic bacteria in dental plaque, without any accompanying dental stain.

Mouthrinse concentrate compositions and aqueous solutions of the present invention are similarly prepared and used by employing 1,12-dodecanedioic diperoxy acid (without or, preferably, with borate buffer components) instead of the magnesium monoperphthalate of the hereinbefore A and B concentrates. For example, aqueous mouthrinses containing 1,12-dodecanedioic diperoxy acid ("DPDA") have the following components:

| | Weight % | |
|---|---|---|
| Component | Composition C | Composition D |
| DPDA | 0.1 | 0.2 |
| Sodium fluoride | 0.034 | 0.067 |
| Boric acid | 0.133 | 0.266 |
| Sodium saccharin | 0.102 | 0.102 |
| Sodium borate[1] | 0.68 | 0.68 |
| 1 N HCl | 1.2 | 1.2 |
| Ethanol | 15 | 15 |
| Water | balance | balance |

[1]Na$_2$B$_4$O$_7$.10H$_2$O

Composition C is prepared as follows: Add 1.0 g of 100% ethanol to a container along with 43.75 mg of a DPDA/boric acid mixture (a hydrate which contains approximately 20% water), and then vortex rapidly for 10 seconds. To this mixture add 14.0 g of a solution containing 9% ethanol, 0.73% sodium borate, 1.3% 1N HCl, 0.11% sodium saccharin, 0.037% sodium fluoride, and 89% water (pH of solution approximately 8.5). Vortex the resulting mixture for another 10 seconds. As prepared, Composition C has an A.O. concentration of approximately 120 ppm. Composition D is similarly prepared using the above procedure but using 87.5 mg of DPDA/boric acid and 0.074% sodium fluoride. As prepared, Composition D has an A.O. concentration of approximately 240 ppm.

Mouthrinse concentrate compositions and aqueous solutions of the present invention are similarly prepared and used by substituting in place of sodium fluoride the compounds stannous fluoride or strontium fluoride as the source of F− fluoride ions.

EXAMPLE 3

Several toothpaste or gel formulations according to the present invention are prepared using procedures taught in U.S. Pat. No. 3,988,433, issued Oct. 26, 1976 to Benedict. Compositions of such formulations are set forth as follows:

| | Weight % |
|---|---|
| Composition A | |
| magnesium monoperphthalate | 5% |
| sodium fluoride | 0.5% |
| triacetin | balance |
| Composition B | |
| magnesium monoperphthalate | 2% |
| sodium fluoride | 0.5% |
| mineral oil (SSF-60) | balance |
| Composition C | |
| magnesium monoperphthalate | 10% |
| stannous fluoride | 2% |
| menthyl acetate and menthene (1:1) | 2% |
| sodium alkyl (C$_{10}$-C$_{12}$) sulfate | 4% |
| diethylether of polyethylene glycol (M.W. 1000) | balance |
| Composition D[1] | |
| Component I: | |

-continued

| | Weight % |
|---|---|
| magnesium monoperphthalate | 10% |
| potassium polyethyoxylated (4) coconut fatty alcohol sulfate | 4% |
| methyl laurate | balance |
| Component II: | |
| dicalcium orthophosphate | 40% |
| eucalyptol | 2% |
| phosphate buffer | 3% |
| sodium fluoride | 2% |
| color | 0.1% |
| methyl laurate | balance |
| Compositon E | |
| DPDA[2] | 5% |
| stannous fluoride | 4% |
| boric acid/borate (buffered to pH = 8.5) | 5% |
| triacetin | balance |
| Composition F | |
| DPDA[2] | 2% |
| sodium fluoride | 0.6% |
| boric acid/borate (buffered to pH = 8.5) | 5% |
| mineral oil (SSF-60) | balance |
| Composition G | |
| DPDA[2] | 10% |
| strontium flouride | 4.2% |
| phosphate buffer (pH = 7.0) | 5% |
| menthyl acetate and menthene (1:1) | 2% |
| sodium alkyl ($C_{10}$–$C_{12}$) sulfate | 4% |
| diethylether of polyethylene glycol (M.W. 1000) | balance |
| Composition H[1] | |
| Component I: | |
| DPDA[2] | 10% |
| potassium polyethoxylated (4) coconut fatty alcohol sulfate | 4% |
| methyl laurate | balance |
| Component II | |
| dicalcium orthophosphate | 40% |
| eucalyptol | 2% |
| boric acid/borate (buffered to pH = 8.5) | 3% |
| sodium fluoride | 1% |
| color | 0.1% |
| methyl laurate | balance |
| Composition I | |
| DPDA[2] | 10% |
| strontium fluoride | 3% |
| boric acid/borate (buffered to pH = 8.0) | 5% |
| menthyl acetate and menthene (1:1) | 2% |
| sodium alkyl ($C_{10}$–$C_{12}$) sulfate | 4% |
| diethylether of polyethyene gycol (M.W. 1000) | balance |

[1]toothpaste compositions formed upon mixing, by coextrusion from separate chambers of a toothpaste tube, components I and II in a 1:1 ratio just prior to use
[2]diperoxy 1,12-dodcanedioic acid Brushing once a day for 30 seconds with 1 ml (approximately 1 gram) of any of the above described toothpastes or gels promotes continued gingival health in persons with healthy gingival tissue by significantly reducing the number of pathogenic bacteria in dental plaque. The compositions are also effective for treating gingivitis. These benefits are obtained without any accompanying dental stain.

EXAMPLE 4

Rat stain and plaque studies are used to evaluate the staining potential and antiplaque efficacy of various formulations. Royalhart Wistar albino rats (Royalhart Laboratory Animals, Inc.; New Hampton, N.Y.) are stratified into groups of 20 animals each (balancing for litter, weight and sex). The test formulations are provided as solutions and are applied topically. Using a micropipetter, 0.25 ml of solution is directed onto the molar teeth of one side of the animal's mouth and another 0.25 ml is applied to the other side of the mouth. Treatments are administered twice daily, five days per week, for a period of three weeks. The first treatment each day is begun at the same time every day, and the second treatment is begun no earlier than six hours after the first treatment.

(a) Molar plaque evaluation:

Two weeks after the treatment phase of the study is initiated, in situ molar plaque is evaluated. This method involves the disclosing (using basic fuschin) of the molar plaque and then estimating the percent coverage of plaque on the mesial surface of the first maxillary molars. This is evaluated by the following scoring system (score and % coverage, respectively): $1 = \leq 10\%$; $2 = \leq 20\%$; $3 = \leq 30\%$, $4 = \leq 40\%$; $5 = \leq 50\%$; $6 = \leq 60\%$; $7 = \leq 70\%$; $8 = \leq 80\%$; $9 = \leq 90\%$; and $10 = \leq 100\%$. The score given to each animal is the sum of the two scores obtained from the first maxillary molars. Standard analysis of variance for treatments are ranked by Newman-Keul's method.

(b) Stain assessments:

At the end of the study the animals are sacrificed and the jaws are cleaned free of tissue by autoclaving for 25 minutes. The cleaned jaws are then air dried for 2 days, after which time the jaws are evaluated for stain. Since the greatest amount of stain accumulates on the mesial surface of the first maxillary molar, an accurate evaluation of stain formation can be determined by scoring only this surface. The percent coverage with stained material of the first surface (mesial) of the first maxillary molar is recorded for both maxillae. The average score per rat is the score used for tabulation and analysis. An intensity factor is assigned to each percent coverage score obtained based on a subjective evaluation of thickness and color intensity; i.e., low = 1; moderate = 2; and heavy = 3. An average intensity score is then determined for each group and is used for tabulation and analysis. Standard analysis of variance with treatments are ranked by Wilcoxon's method.

(c) Evaluation

The following formulations are evaluated in one study ("Study #1") versus a deionized water control:
(1) 0.5% magnesium monoperphthalate in carbonate/citrate buffer;
(2) 0.5% magnesium monoperphthalate + 500 ppm NaF in carbonate/citrate buffer;
(3) 0.5% magnesium monoperphthalate + 500 ppm sodium monofluorophosphate in carbonate/citrate buffer; and
(4) 0.1% chlorhexidine digluconate (hereinafter "chlorhexidine").

TABLE 2

Rat stain and molar plaque results for Study #1

| Treatment Formulation | Mean Stain Score Per Rat | Mean Plaque Score Per rat | Percent Plaque Reduction |
|---|---|---|---|
| Deionized water | 14.6 | 8.25[3] | —[3] |
| 0.5% MMPP[1] + 500 ppm NaF | 32.5[2] | 2.05 | 75 |
| 0.5% MMPP[1] | 44.1 | 0.90 | 89 |
| 0.5% MMPP[1] + 500 ppm MFP[4] | 47.6 | 1.85 | 78 |
| 0.1% chlorhexidine | 56.1 | 0.40 | 95 |

[1]MMPP = magnesium monoperphthalate (in carbonate/citrate buffer)
[2]Not significantly different from deionized water (p < 0.05).
[3]Significantly different from all other formulations (p < 0.05).
[4]MFP = sodium monofluorophosphate Test results from Study #1 for stain and molar plaque for these formulations are provided in Table 2. Of these formulations, only the magnesium monoperphthalate/NaF formulation is not significantly different from the control with regard to stain. Furthermore, all the formulations significantly reduce plaque relative to the control. Thus, it can be concluded that the stain benefit for the magnesium monoperphthalate/NaF formulation is achieved while providing anti-plaque efficacy.

Finally, the following formulations are evaluated in another study ("Study #2") versus a deionized water control:

(1) 0.5% magnesium monoperphthalate in carbonate/citrate buffer;
(2) 0.5% magnesium monoperphthalate + 500 ppm NaF in carbonate/citrate buffer;
(3) 0.12% chlorhexidine; and
(4) 500 ppm NaF followed within 10 min. by 0.12% chlorhexidine.

TABLE 3
Rat stain and molar plaque results for Study #2

| Treatment Formulation | Mean Stain Score Per Rat | Mean Plaque Score Per Rat | Percent Plaque Reduction |
|---|---|---|---|
| Deionized water | 8.6 | 7.9(3) | —(3) |
| 0.5% MMPP(1) + 500 ppm NaF | 13.6(2) | 1.5 | 81 |
| 0.5% MMPP(1) | 21.5 | 1.5 | 81 |
| 0.12% chlorhexidine | 39.9 | 0.6 | 92 |
| 0.12% chlorhexidine + 500 ppm NaF | 44.3 | 1.2 | 85 |

(1)MMPP = magnesium monoperphthalate (in carbonate/citrate buffer)
(2)Not significantly different from deionized water (p < 0.05)
(3)Significantly different from all other formulations (p < 0.05)

Test results from Study #2 for stain and molar plaque for these formulations are provided in Table 3. These results are consistent with the results of Study #1. In addition, the chlorhexidine and chlorhexidine/NaF formulations produce essentially the same stain, with the chlorhexidine/NaF formulation being directionally more staining.

What is claimed is:

1. A pharmaceutical composition suitable for treating or preventing dental plaque, or gingival, or periodontal diseases of the oral cavity with reduced staining of teeth or dentures, which composition comprises:
   (a) from about 0.001% to about 99.9% of an organic monoperphthalic peroxy acid-based antigingivitis agent selected from 1,12-dodecanedioic peroxy acid and its derivatives, monoperphthalic acid and its derivatives, and the pharmaceutically-acceptable salts and esters thereof;
   (b) from about 0.001% to about 10% of a source of F− fluoride ions, which source essentially completely dissociates in aqueous solution to provide free F− fluoride ions in solution; and
   (c) a pharmaceutically-acceptable carrier suitable for delivering said antigingivitis agent and said fluoride ion source to the oral cavity.

2. A pharmaceutical composition for oral use according to claim 1, wherein the organic monoperphthalic peroxy acid-based antigingivitis agent is selected from:
   (a) unsubstituted or substituted 1,12-dodecanedioic peroxy acids, wherein the 1,12-dodecanedioic peroxy acid substituents are selected from the group consisting of straight or branched chain alkyl groups having from 1 to about 6 carbon atoms, phenyl, benzyl, chloro, fluoro, nitro, trifluoromethyl, trialkylammonium, —CO₂ H, —CO₃ H, and combinations of such substituents; the pharmaceutically-acceptable salts and esters of said peroxy acids; and combinations of these antigingivitis agents; and
   (b) substituted or unsubstituted monoperphthalic acid having the general structure:

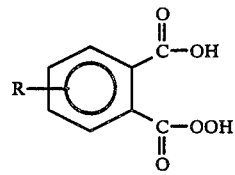

wherein R is one or more substitutents independently selected from the group consisting of hydrogen, straight or branched chain saturated alkyl having from 1 to about 20 carbon atoms, phenyl, benzyl, naphthyl, chloro, fluoro, nitro, sulfonate, trifluoromethyl, —NR'₃, —CO₂ H, —CO₃ H, —O-COR', and —OR'; with each R' being independently selected from straight or branched chain saturated alkyl having from 1 to about 6 carbon atoms; the pharmaceutically-acceptable salts and esters of said acids; and combinations of these antigingivitis agents.

3. A pharmaceutical composition for oral use according to claim 2 wherein the organic monoperphthalic peroxy acid-based antigingivitis agent is selected from unsubstituted peroxy 1,12-dodecanedioic acid, unsubstituted monoperphthalic acid, the pharmaceutically-acceptable salts and esters of these acids, and combinations of these antigingivitis agents; and wherein further the source of F− fluoride ions is selected from sodium fluoride, stannous fluoride, strontium fluoride, indium fluoride, amine fluorides, and combinations thereof.

4. A pharmaceutical composition for oral use according to claim 3 wherein:
   (a) the organic monoperphthalic peroxy acid-based antigingivitis agent is selected from diperoxy 1,12-dodecanedioic acid, monoperoxy 1,12-dodecanedioic acid, the pharmaceutically-acceptable salts and esters of these acids, and combinations of these antigingivitis agents;
   (b) the source of F− fluoride ions is sodium fluoride; and
   (c) the pharmaceutically-acceptable carrier comprises one or more components selected from effervescing agents, surfactants, chelating agents, ethyl alcohol, water, flavorants, sweeteners, humectants, sudsing agents, dental abrasive polishing materials, thickening agents, coloring agents, emulsifying agents, boron-containing aliphatic peroxy acid-stabilizing agents, buffering agents, and combinations of these components.

5. A pharmaceutical composition for oral use according to claim 4 which comprises a boron-containing, aliphatic monoperphthalic peroxy acid-stabilizing agent selected from boric acid, pyroboric acid, boron-containing materials which generate boric acid when contacted with water, boron-containing materials which generate pyroboric acid when contacted with water, the pharmaceutically-acceptable salts and esters thereof these stabilizing agents, and combinations of these stabilizing agents.

6. A pharmaceutical composition suitable for treating or preventing dental plaque, or gingival, or periodontal diseases of the oral cavity with reduced staining of teeth or dentures, which compositions comprise:
  (a) from about 0.01% to about 50% of an organic monoperphthalic peroxy acid-based antigingivitis agent selected from substituted or unsubstituted monoperphthalic acids having the general structure:

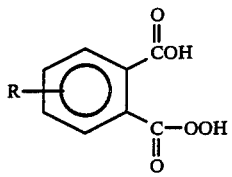

wherein R is one or more substitutents independently selected from the group consisting of hydrogen, straight or branched chain saturated alkyl having from 1 to about 20 carbon atoms, phenyl, benzyl, naphthyl, chloro, fluoro, nitro, sulfonate, trifluoromethyl, $-NR'_3$, $-CO_2H$, $-CO_3H$, $-OCOR'$, and $-OR'$; with each R' being independently selected from straight or branched chain saturated alkyl having from 1 to about 6 carbon atoms; the pharmaceutically-acceptable salts and esters of said acids; and combinations of these antigingivitis agents;
  (b) from about 0.001% to about 10% of a source of $F^-$ fluoride ions, which source essentially completely dissociates in aqueous solution to provide free $F^-$ fluoride ions in solution; and
  (c) a pharmaceutically-acceptable carrier suitable for delivering said antigingivitis agent and said fluoride ion source to the oral cavity.

7. A pharmaceutical composition for oral use according to claim 6 wherein:
  (a) the organic monoperphthalic peroxy acid-based antigingivitis agent is monoperphthalic acid, or a pharmaceutically-acceptable salt or ester thereof;
  (b) the source of $F^-$ fluoride ion is selected from sodium fluoride, stannous fluoride, strontium fluoride, indium fluoride, amine fluorides, or combinations thereof; and
  (c) the pharmaceutically-acceptable carrier comprises one or more components selected from effervescing agents, surfactants, chelating agents, ethyl alcohol, water, flavorants, sweeteners, humectants, sudsing agents, dental abrasive polishing materials, thickening agents, coloring agents, emulsifying agents, buffers, and combinations of these components.

8. A pharmaceutical composition suitable for treating or preventing dental plaque, or gingival, or periodontal diseases of the oral cavity with reduced staining of teeth or dentures, which composition comprises:
  (a) from about 0.1% to about 35% of magnesium monoperphthalate antigingivitis agent;
  (b) from about 0.001% to about 5% of a sodium fluoride anticaries agent; and
  (c) a pharmaceutically-acceptable carrier for said magnesium monoperphthalate and said anticaries agent.

9. A pharmaceutical composition for oral use according to claim 8, wherein the pharmaceutically-acceptable carrier comprises one or more components selected from an effervescing agent, surfactant, chelating agent, ethyl alcohol, water, flavorants, sweeteners, humectants, sudsing agents, dental abrasive polishing materials, thickening agents, coloring agents, emulsifying agents, buffers, and combinations of these components.

10. A pharmaceutical composition for oral use according to claim 9 comprising a citric acid chelating agent.

11. A method for treating or preventing dental plaque, or gingival, or periodontal diseases of the oral cavity in humans or lower animals with reduced staining of the teeth or dentures, said method comprising topically applying to the oral surfaces of humans or lower animals a safe and effective amount of a composition according to claim 1.

12. A method for treating or preventing dental plaque, or gingival, or periodontal diseases of the oral cavity in humans or lower animals with reduced staining of the teeth or dentures, said method comprising topically applying to the oral surfaces of humans or lower animals a safe and effective amount of a composition according to claim 2.

13. A method for treating or preventing dental plaque, or gingival, or periodontal diseases of the oral cavity in humans or lower animals with reduced staining of the teeth or dentures, said method comprising topically applying to the oral surfaces of humans or lower animals a safe and effective amount of a composition according to claim 3.

14. A method for treating or preventing dental plaque, or gingival, or periodontal diseases of the oral cavity in humans or lower animals with reduced staining of the teeth or dentures, said method comprising topically applying to the oral surfaces of humans or lower animals a safe and effective amount of a composition according to claim 4; wherein said safe and effective amount is such that the concentration of the available oxygen generated by the antigingivitis agent is in the range of from about 1.2 ppm to about 12,000 ppm.

15. A method for treating or preventing dental plaque, or gingival, or periodontal disease of the oral cavity in humans or lower animals with reduced staining of the teeth or dentures, said method comprising topically applying to the oral surfaces of humans or lower animals a safe and effective amount of a composition according to claim 5; wherein said safe and effective amount is such that the concentration of the available oxygen generated by the antigingivitis agent is in the range of from about 1.2 ppm to about 1,200 ppm, and wherein further said composition has a pH within the range of from about 7.0 to about 9.0.

16. A method for treating or preventing dental plaque, or gingival, or periodontal diseases of the oral cavity in humans or lower animals with reduced staining of the teeth or dentures, said method comprising topically applying to the oral surfaces of humans or lower animals a safe and effective amount of a composition according to claim 6.

17. A method for treating or preventing dental plaque, or gingival, or periodontal diseases of the oral cavity in humans or lower animals with reduced staining of the teeth or dentures, said method comprising topically applying to the oral surfaces of humans or lower animals a safe and effective amount of a composition according to claim 7; wherein said safe and effective amount is such that the concentration of the available oxygen generated by the antigingivitis agent is in the range of from about 60 ppm to about 6000 ppm.

18. A method for treating or preventing dental plaque, or gingival, or periodontal diseases of the oral cavity in humans or lower animals with reduced staining of the teeth or dentures, said method comprising topically applying to the oral surfaces of humans or lower animals a safe and effective amount of a composition according to claim 8.

19. A method for treating or preventing dental plaque, or gingival, or periodontal diseases of the oral cavity in humans or lower animals with reduced staining of the teeth or dentures, said method comprising topically applying to the oral surfaces of humans or lower animals a safe and effective amount of a composition according to claim 9; wherein said safe and effective amount is such that the concentration of the available oxygen generated by the antigingivitis agent is in the range of from about 240 ppm to about 3000 ppm.

20. A method for treating or preventing dental plaque, or gingival, or periodontal diseases of the oral cavity in humans or lower animals with reduced staining of the teeth or dentures, said method comprising topically applying to the oral surfaces of humans or lower animals a safe and effective amount of a composition according to claim 10; wherein said safe and effective amount is such that the concentration of available oxygen generated by the magnesium monoperphthalate is in the range of from about 600 ppm to about 1800 ppm; and wherein further said composition has a molar ratio of citric acid chelating agent to magnesium monoperphthalate of at least about 1:1.

* * * * *